United States Patent
Sabee

Patent Number: 4,618,384
Date of Patent: Oct. 21, 1986

[54] METHOD FOR APPLYING AN ELASTIC BAND TO DIAPERS

[76] Inventor: Reinhardt N. Sabee, 728 S. Summit St., Appleton, Wis. 54911

[21] Appl. No.: 530,544

[22] Filed: Sep. 9, 1983

[51] Int. Cl.⁴ .......................... B31F 1/22; B65C 1/00
[52] U.S. Cl. .................................. 156/205; 156/214; 156/244.11; 156/244.22
[58] Field of Search ............... 156/164, 206, 216, 202, 156/160, 205, 229, 290, 291, 292, 297, 208, 210, 214, 244.18, 244.22, 244.11, 244.15, 244.27; 427/275

[56] References Cited

U.S. PATENT DOCUMENTS

| | | | |
|---|---|---|---|
| 4,081,301 | 3/1978 | Buell | 156/216 |
| 4,227,952 | 10/1980 | Sabee | 156/164 |
| 4,379,016 | 4/1983 | Stemmier et al. | 156/164 |
| 4,543,099 | 9/1985 | Bunnelle | 156/164 |

Primary Examiner—Edward Kimlin
Assistant Examiner—Louis Falasco
Attorney, Agent, or Firm—Fuller, House & Hohenfeldt

[57] ABSTRACT

Methods for applying elastic bands to webs to form diapers includes extruding a thermoplastic rubber onto the web with the rubber self bonding or being secured by adhesive. The extruder head is movable to form elastic with a varying cross-section and to provide non-linear deposition patterns to provide a diaper with a close comfortable fit.

11 Claims, 26 Drawing Figures

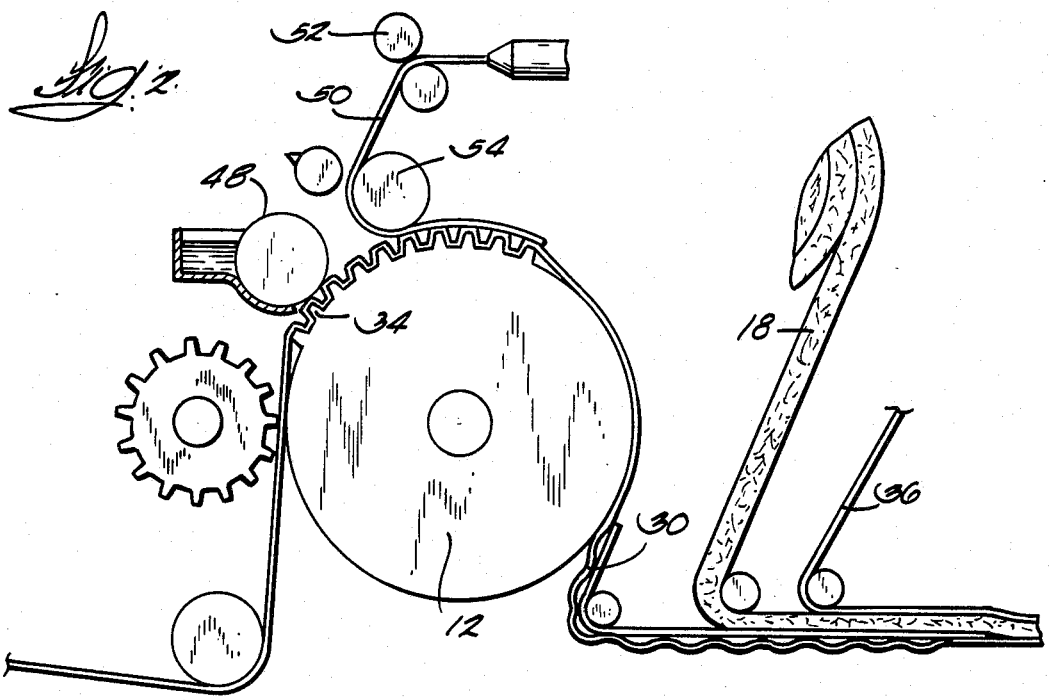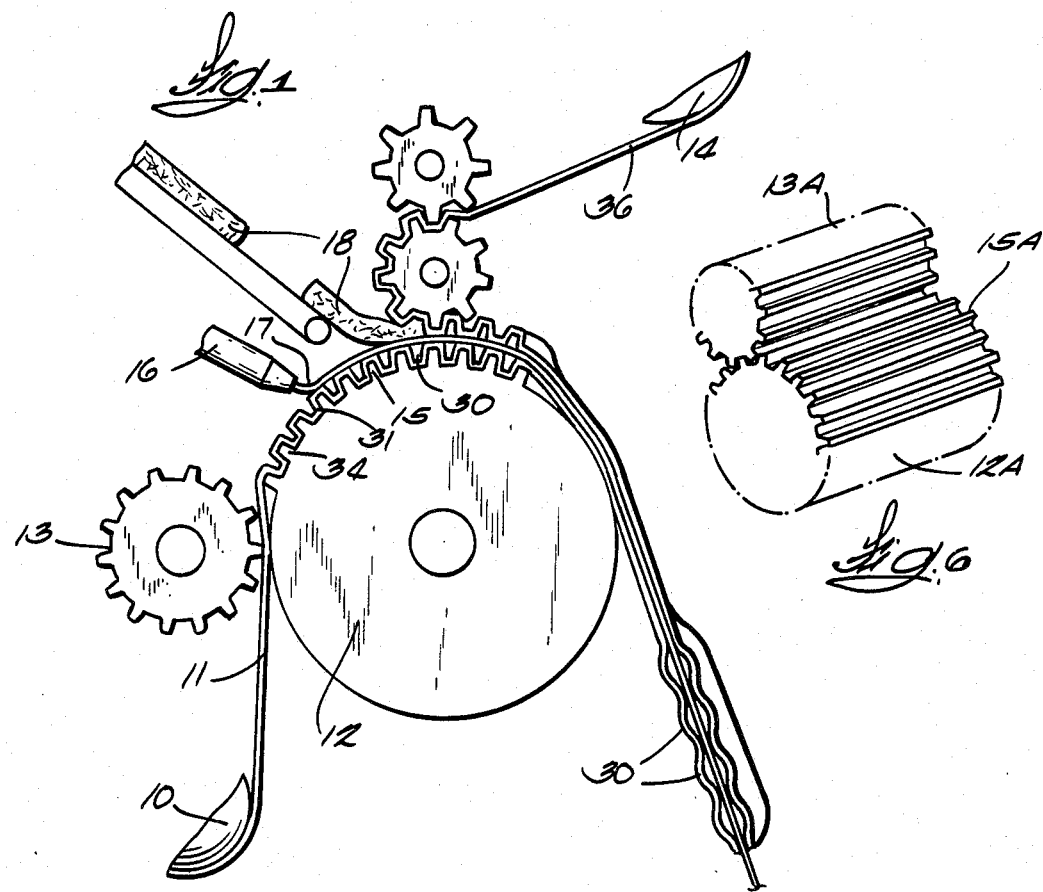

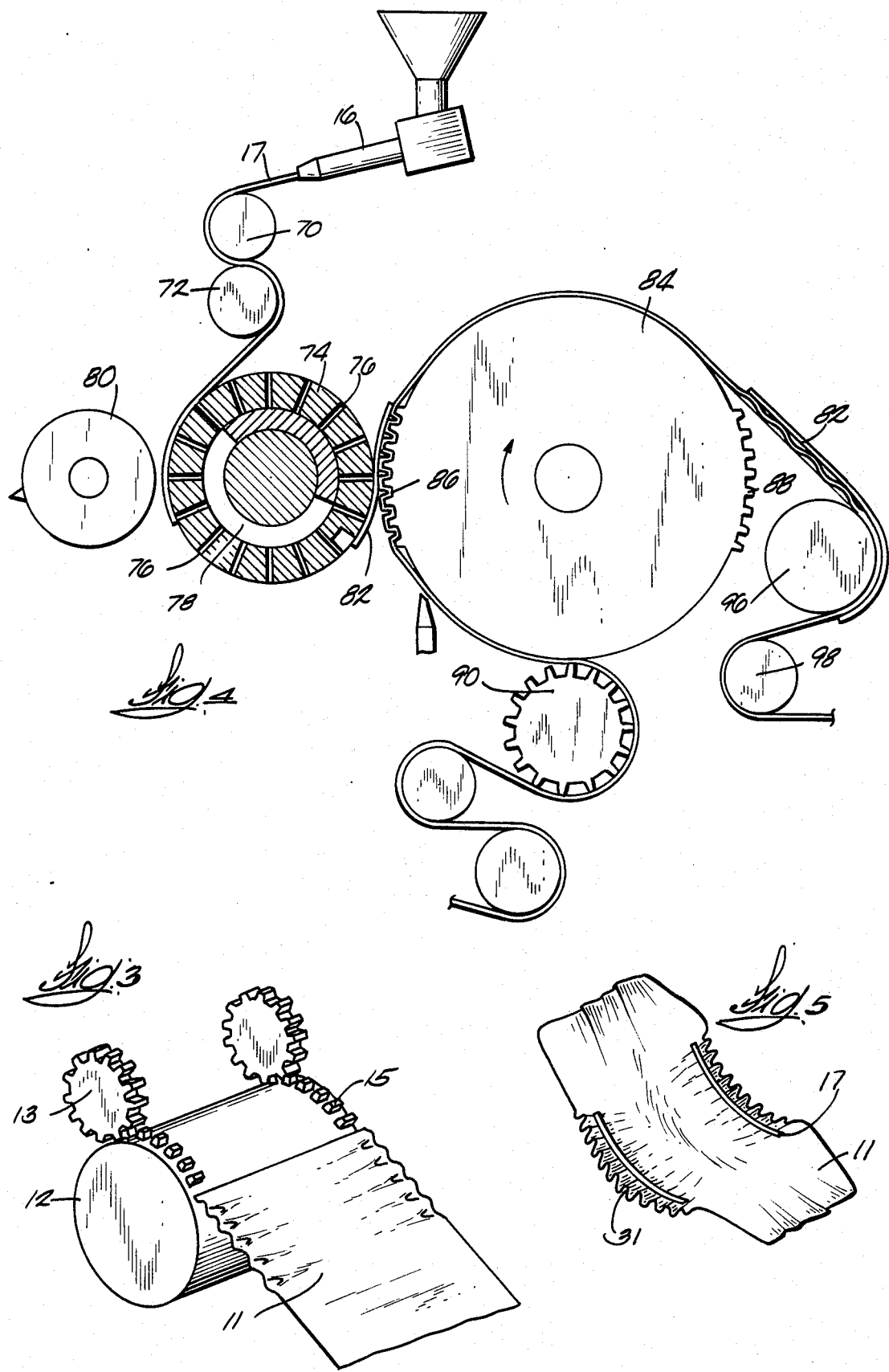

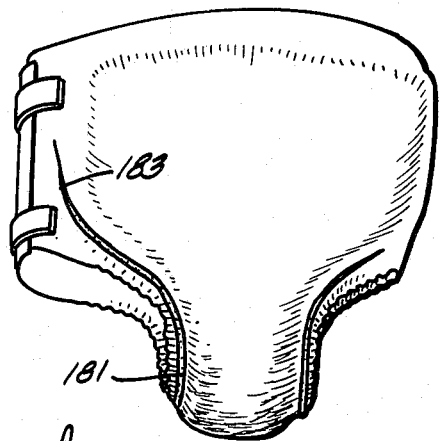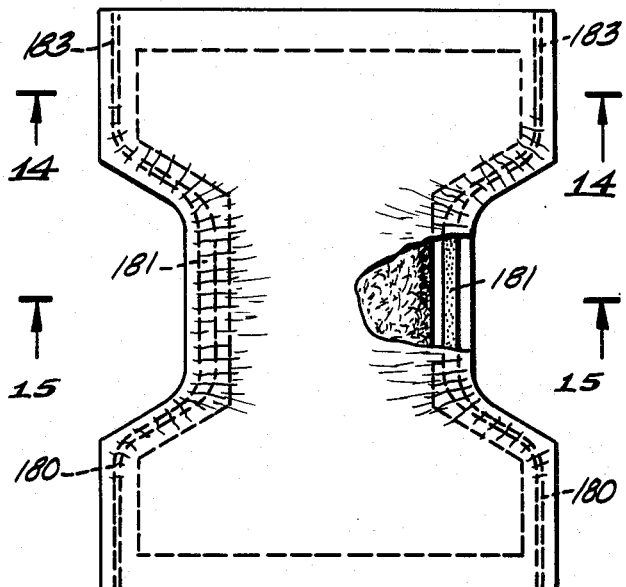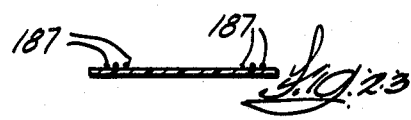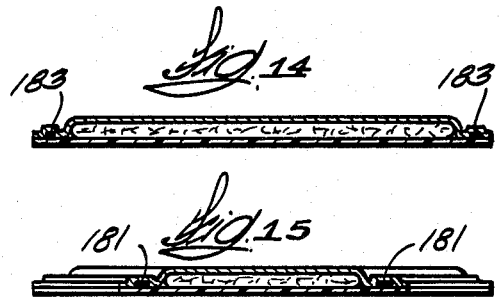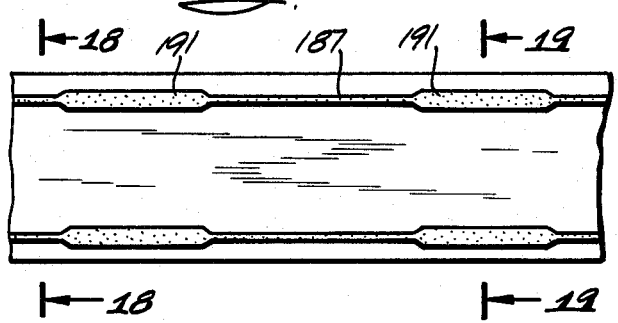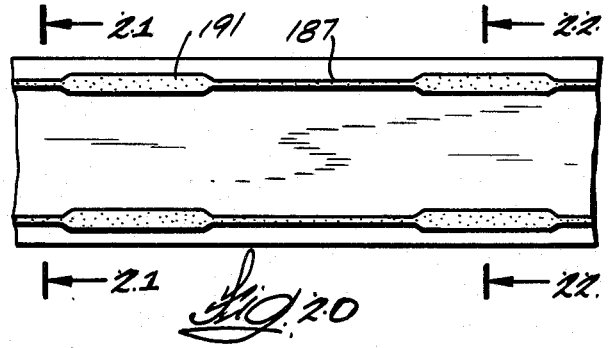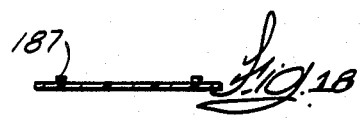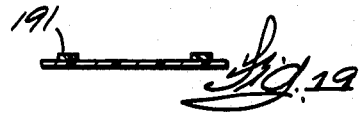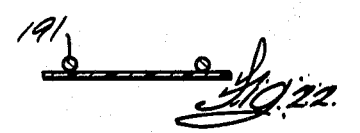

METHOD FOR APPLYING AN ELASTIC BAND TO DIAPERS

BACKGROUND OF THE INVENTION

The invention relates to method and apparatus for making diapers with elastic bands in the leg contracting zone of the diaper. U.S. Pat. No. 4,081,301 and my U.S. Pat. No. 4,227,952 are illustrative of patents which show diaper making apparatus with elastic band applying stations.

In prior art techniques the elastic band is stretched prior to application to the backing or facing sheet. Methods that use or apply elastic bands in a stretched condition are not suitable for applying an extruded elastomeric band in a heat softened state directly to the backing or facing.

With prior art techniques the elastic strips or ribbons have a uniform cross-section throughout their length. Hence, when relaxed and upon application of the diaper to the baby, have the same tension throughout the crotch length. As a result, some portions of the elastic member cause a high degree of stress concentration that may result in pinching, indenting, marking and irritation of the baby's skin.

The methods of applying pre-formed elastic band material from bulk containers of elastic band also have associated problems involving splicing, threading, alignment and application to webs. In addition, uniformity in tension during assembly is also a problem. The difficulties in manipulating pre-formed elastic ribbons also limit the shapes and patterns of elastic members as well as their placement on the diaper. Normally it is difficult to place an elastic member under tension on a web in other than a straight line path because of the tendency of the stretched elastic member to return to a straight line.

U.S. Pat. No. 4,379,016 discloses the application of or formation in situ of an elastic ribbon by spraying across folds and filling the folds with the sprayed material. This arrangement requires self bonding or adherence of the elastic material to the web and may limit the web materials which can be utilized and which will bond with the sprayed ribbon.

In addition to the difficulties in handling and applying pre-formed elastic ribbons the cost of elastic ribbon material is exceedingly high. My prior U.S. Pat. No. 4,227,952 has succeeded in reducing the cost of the length of elastic band employed to about 50% of an elastic ribbon, the full length of a diaper.

SUMMARY OF THE INVENTION

The present invention provides an improved method of applying elastic ribbon to provide an elasticized crotch area in a diaper which enables applying elastic bands in other than straight lines to form diapers with an improved fit or improved body conformity without undue pressure on the wearer.

More specifically, the method of the present invention relates to extruding at high viscosity an elastic band or ribbon in a non-stretched condition across corrugations on a web and securing the elastic to the peaks rather than the peaks and valleys as disclosed in U.S. Pat. No. 4,379,016. In the various methods disclosed the web and elastic ribbon are secured by heat sealing, heat sealing and additionally adhesives or solely adhesives. In none of the embodiments are the valleys of the corrugations filled with the elastic ribbon material.

The extruded elastic band is applied longitudinally over transverse pleats or corrugations in the margin of the facing or backing sheet. When the diaper is stretched tightly in use about the baby, the pleats will be opened or pulled apart and the elastic ribbon will be under tension and provide a grip and fluid seal on the user. In one embodiment the elastic ribbon is formed by extruding the ribbon at the elastic band application station directly unto and self bonded to corrugations on the diaper facing or backing sheet. Alternatively, the extruded elastic can be pre-cooled with chill rollers and adhesive applied prior to assembly of the elastic ribbon on the diaper.

The present invention also provides for controlled extrusion of the elastic ribbon. In accordance with the invention, the extruder and extruder pump are controlled to vary the volume of extruded elastic to provide a thick ribbon in the crotch area and a thinner ribbon in waistband portions. This can result in substantial savings in material. Also the extruder can be stationary or moved in a cyclic path for a pattern deposition of the elastic ribbon. Hence a pattern for an elastic ribbon which is complimentary to the hour glass shape of the diaper rather than straight is easily accomplished to provide for a better fitting diaper. The appropriate patterns or configurations of the elastic band or groups of bands and the cross-sectional areas for the elastic ribbon can be selected to provide different constricting tension in various parts of the diaper, both for purpose of achieving maximum comfort and also to provide a good fluid seal. By improving the fit, the tension can be decreased to provide for more comfort to the wearer.

Further objects, advantages and features of the invention will be apparent from the disclosure.

DESCRIPTION OF THE DRAWINGS

FIG. 1 is a diagrammatic perspective view illustrating apparatus for practicing the method of the invention.

FIG. 2 is a diagrammatic view of apparatus for practicing a modified method.

FIG. 3 is a diagrammatic perspective view of the pleating rollers.

FIG. 4 is a diagrammatic view of apparatus for practicing a further modified method.

FIG. 5 is a perspective view of a diaper made by the process illustrated in FIG. 3.

FIG. 6 is a perspective view of the corrugating rollers which corrugate the entire width of the backing or facing sheet.

FIG. 13 is a plan view of a diaper having an elastic band complimentary and shaped to the edge margin.

FIG. 14 is a sectional view along line 14—14 of FIG. 13.

FIG. 15 is a sectional view along line 15—15 of FIG. 13.

FIG. 16 is a perspective view of the diaper illustrated in FIGS. 13, 14 and 15.

FIG. 17 is a plan view of a web with an elastic band extruded in a straight line with a varying cross-section.

FIG. 18 is a sectional view along line 18—18 of FIG. 17.

FIG. 19 is a sectional view along line 19—19 of FIG. 17.

FIG. 20 is a plan view of a web with an elastic band applied in the round cross-section.

FIG. 21 is a sectional view along line 21—21 of FIG. 20.

FIG. 22 is a sectional view along line 22—22 of FIG. 20.

FIG. 23 is a diagrammatic sectional view showing three cylindrical beads which form spaced elastic ribbons.

DESCRIPTION OF THE PREFERRED EMBODIMENT

Figure 7:
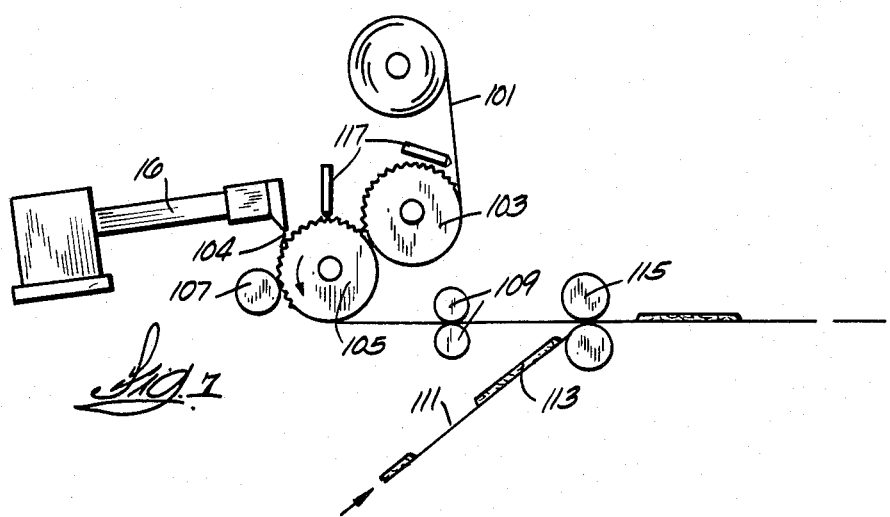
FIG. 7 is a diagrammatic view side elevation view of apparatus for extruding a ribbon directly unto a web for self bonding to the web.

Although the disclosure hereof is detailed and exact to enable those skilled in the art to practice the invention, the physical embodiments herein disclosed merely exemplify the invention which may be embodied in other specific structure. The scope of the invention is defined in the claims appended hereto.

In the drawings, FIG. 1 shows a backing or parent roll 10 for supplying a web 11, corrugating rolls 12 and 13 and a facing or backing supply roll 14. FIG. 1 also discloses a thermoplastic extruder 16 which extrudes a band or ribbon of molten elastomer 17 which forms the elastic ribbon for the crotch area.

Thermoplastic rubbers suitable for extrusion, such as Shell Chemical Company's KRATON 2000 and 3000 series and GX-2701, are thermoplastic rubbers which can be employed for the elastic bands. These rubbers combine the properties of vulcanized elastomers and the processing advantages of thermoplastics. Standard thermoplastic processing equipment can be used to form the rubber extrudates. The present invention, however, is not limited to Shell Chemical Company's KRATON thermoplastic rubbers. Any elastomeric thermoplastic material which is soft, flexible, and elastic is satisfactory.

Means can also be provided for delivery of a string of absorbent pads 18 to the ribbon-web assembly station. In practice, in the manufacture of diapers two spaced elastic ribbons are extruded for both sides of the diaper crotch area, as illustrated in FIG. 3. However, multiple extrusions may be utilized as in FIG. 23.

In operation of the apparatus disclosed in FIG. 1, the backing sheet 11 is drawn off the parent roll 10 by the pleating rollers 12 and 13. The toothed segment 15 on roller 12 and the teeth on roller 13 provide spaced, pleated or corrugated zones in the web 11 at the side margins only of the diaper, as illustrated in FIG. 3. Optionally, pleats can be formed for the entire width of the web by corrugating rollers, such as those illustrated in FIG. 6. The extruded elastomeric ribbon 17 is applied to the peaks 34 of the pleats 31 under a first tension or substantially no tension. The molten ribbon 17 adheres to the peaks and this condition is maintained to afford cooling to afford a good bond before there is any further processing. The string of absorbent pads 18 can be fed into this system prior to application of a facing sheet 36 from the roll 14. The facing sheet 36 is similarly corrugated and superimposed on the backing web and elastic ribbon 17. When the lamina is withdrawn from the roll 12 at a second tension higher than the first tension, the pleats may be flattened by the second tension which is required for moving the web from the roll 12 to further stations in the diaper manufacturing process. The pleats are shown at their maximum amplitude in FIG. 1 upon the roller, with a lesser amplitude as the web and pleats are withdrawn at the second tension.

FIG. 2 shows a modified embodiment of the method of the invention in which the extruded ribbon 50 passes through two sets of chill rolls 52 and 54 before it is applied to the peaks 34 of the pleats or corrugations under a first or low tension. In this embodiment adhesive is applied to the peaks by an adhesive applicator 48 prior to the application of the ribbon 50 to the peaks. As the ribbon-web lamina is withdrawn from roll 12, the pleats are drawn out as illustrated, by the tension on the ribbon-web lamina. Absorbent pad material 18 can then be applied with a facing or backing sheet 36 also added.

FIG. 4 shows a further modified embodiment in which the ribbon 17 extruded by extruder 16 is chilled by chill rolls 70 and 72 and fed to a vacuum drum 74, with a plurality of vacuum passages 76 communicating with a vacuum manifold 78. The chilled ribbon 17 is conveyed past a rotary knife cutter 80 which cuts the ribbon to discrete lengths 82 which are conveyed to the corrugating drum 84 which has corrugating tooth segments 86 and 88 which mesh with spaced corrugating roller 90 to form the pleats. The lengths 82 are applied with little or no tension or stretch. The web-ribbon lamina is withdrawn by take-up rolls 96 and 98. FIG. 5 is illustrative of a diaper formed by the process of FIG. 4.

FIG. 6 illustrates the rollers 13 and 12 which span the width of the backing sheet and facing sheet 11 and 36 to corrugate the entire width of the diaper at the places where the elastic ribbon is applied. If the rollers do not have teeth completely around their periphery they will form groups of corrugations longitudinally spaced.

FIG. 7 is a diagrammatic view showing an extruder 16 which extrudes a ribbon 104 directly onto the web 101 which can be a facing or backing sheet after it has been corrugated by corrugating rollers 103 and 105. The ribbon 104 is at a first tension or substantially no tension when applied to the web. A chill roll 107 cools the extruded ribbon to solidify the ribbon before the ribbon-web lamina is withdrawn from roll 105 by draw rollers 109. The other of a backing or facing sheet 111 carries spaced absorbent pads 113 to combine with the facing or backing sheet 101 containing the elastic at the station having combining rolls 115. In this embodiment of the apparatus, adhesive to secure the ribbon 104 can be applied by one or more adhesive applicators 117 directly to the web 101. If the extruded ribbon is not cooled it can be self-bonded to the web without adhesive.

Figure 8:
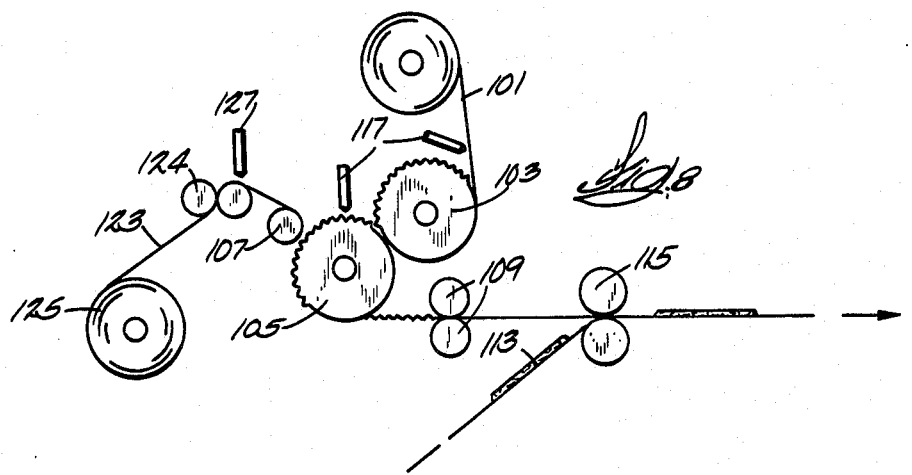
FIG. 8 is a diagrammatic view of apparatus for applying a pre-formed elastic ribbon with adhesive applied in an unstretched condition on a web.

In the diagrammatic view shown in FIG. 8, preformed elastic ribbon on a parent or storage roll 125 is drawn off the roll by draw rollers 124. An elastomeric hot melt adhesive is applied to the ribbon by an applicator 127. The web 101 can also have adhesive applied by applicators 117. As with the prior embodiment, draw rolls 109 apply a second tension and flatten the corrugations and stretch the elastic as the web-elastic ribbon lamina is withdrawn.

Figure 9:
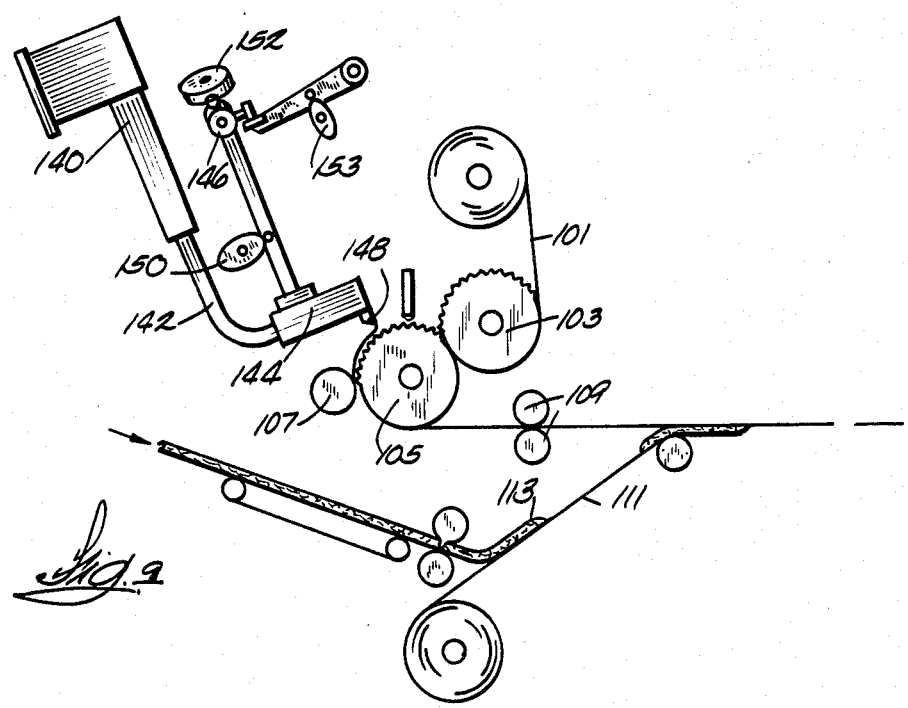
FIG. 9 is a diagrammatic view of an extruder nozzle which can be moved to vary the cross section of elastic ribbon and vary the laydown pattern and in which the elastic is extruded directly unto the web.

In the FIG. 9 embodiment an extruder 140 is provided with a heated flexible tube 142 and a gear pump 144 which includes a support or sliding hub 146 which provides for movement of the extrusion die 148 in a direction transverse of the web or in the cross machine direction. A cam 150 affords movement of the extrusion die fore and aft of the web. A cam 152 can move the die 148 transversely of the web, and cam 153 can move the die 148 toward and away from the web. This can change the thickness and cross-section of the ribbon and the pattern in which it is laid on the web to provide an elastic ribbon pattern which conforms to the outline of the hour glass shaped diaper as illustrated in FIG. 13.

Figure 10:
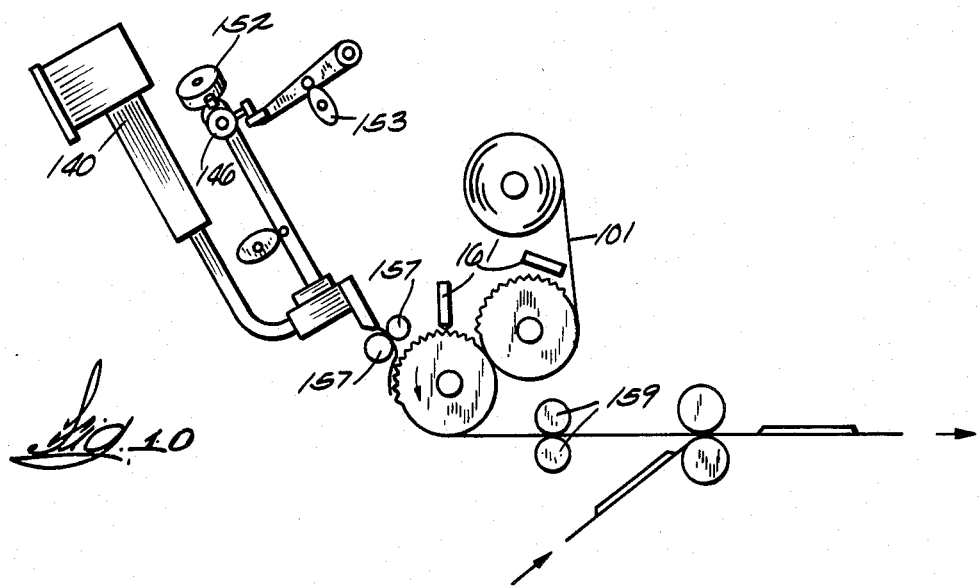
FIG. 10 is a diagrammatic view similar to FIG. 9 in which the ribbon of elastic is chilled prior to deposition.

FIG. 10 is similar to FIG. 9 except for chilled squeeze rollers 157 which chill the elastic ribbon before application to the web 101. Adhesive is applied by an adhesive applicator 161. In FIG. 10, the elastic ribbon is applied in a substantially unstretched condition at a first tension.

Figure 11:
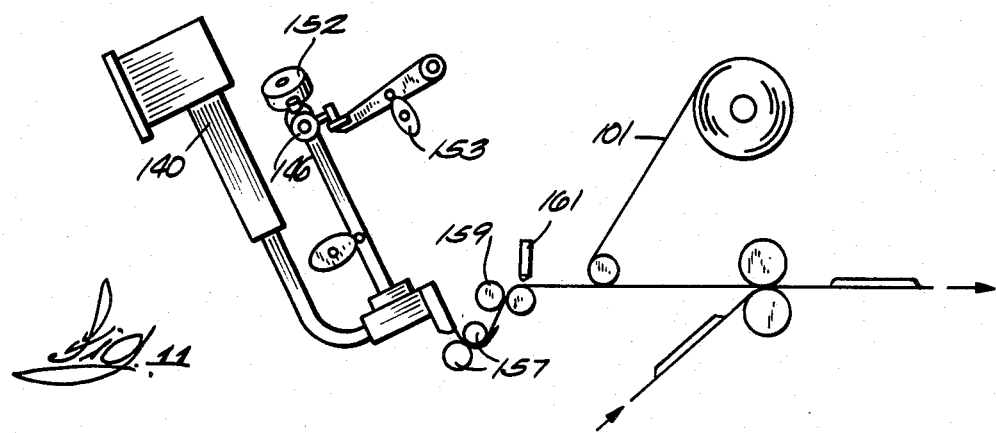
FIG. 11 is a diagrammatic view similar to FIG. 10 in which adhesive is applied to the ribbon in advance of application to the diaper.

FIG. 11 is similar to FIG. 10 except for stretch rollers 159, and adhesive is applied by an adhesive applicator 161 whereupon the elastic ribbon is applied under tension greater than the first tension of FIG. 10 to a web 101 rather than in a substantially unstretched condition.

Figure 12:
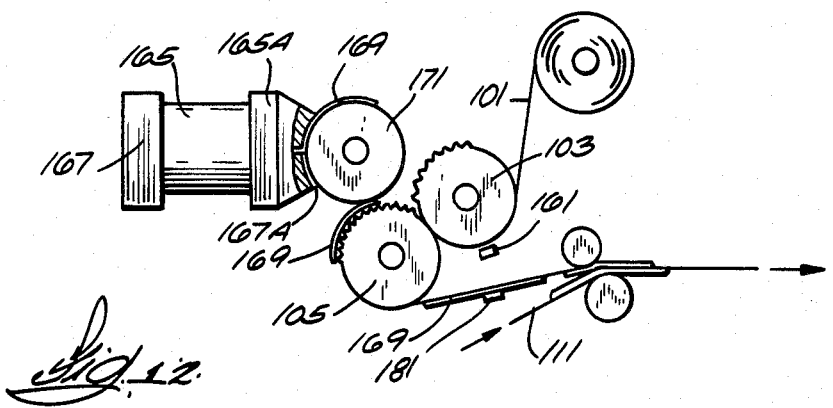
FIG. 12 is a diagrammatic view in which discrete elastic ribbon lengths are extruded and applied to the diaper web.
Figure 12A:
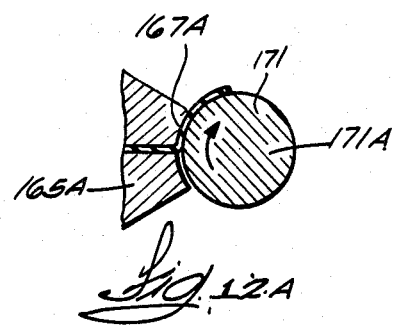
FIG. 12A is a diagrammatic sectional view of an extruder head.

In FIG. 12, the apparatus includes an intermittent and variable pump 165 associated with an extruder 167 which extrudes discrete strips 169 of elastic ribbon onto a temperature controlled non-stick Teflon roll 171 which transfers the strip 169 to the corrugating rollers 105 and 103. The extruder head illustrated in FIG. 12 includes (FIG. 12A) the roller 171 which has a periphery 171A which nests in a complementary curved surface 167A of die 165A. This arrangement prevents the build-up of extrudate at the die lip when flow of melt is interrupted. The web 101 has adhesive applied by an applicator 161 prior to corrugation. Adhesive applicator 181 also applies adhesive to the ribbon-web lamina before the web 111 is assembled therewith.

The extruder die may be reciprocated laterally across the web which, when combined with variable pumping, will produce elastic members of variable cross-section and laydown patterns. Although FIGS. 7–12 have been discussed relative to the application of one elastic band to a web when diapers are being formed, at least two spaced elastic ribbons or groups would be applied to the web.

As illustrated in FIGS. 13 through 16, with apparatus such as that illustrated in FIGS. 9, 10, and 11, where the feed of the pump and extruder dies can be controlled or moved, a cross-section of various sizes can be selected. An elastic ribbon 180 is illustrated in FIG. 13 with relatively large cross-section of ribbon at 181 in the crotch and relatively small cross-section at 183 in the waistband portions can be applied. This can result in substantially increased comfort for the wearer.

FIG. 17 shows diaper waistband areas 187 with the adjoining crotch areas 191 having an elastic ribbon with a larger cross-section which affords greater tension for a tighter fit in the crotch.

FIGS. 20, 21 and 22 show elastic ribbon with a round or circular cross-section with greater diameter in the crotch area than in the waistband portions. FIG. 23 shows three side-by-side small diameter beads 187 which form the elastic ribbons.

In addition to extruding continuously throughout the length of the web, the elastic can be extruded intermittently so that there is elastic only in the crotch portion. This will result in significant savings of elastic material. By having the elastic band extend outwardly as shown in FIGS. 13 and 16, this diaper structure encircles the thigh more completely rendering or providing more effective seal with a reduced tension or constriction on the thigh. This significantly reduces the indenting or marking of the skin and the possibility of irritation to the wearer.

It is apparent that various advantages are achieved with the present invention. Material is saved by decreasing the cross-sectional area of the elastic as the elastic approaches the waistband area. This gradual reduction also avoids a sharp line of demarkation from high tension portions to relaxed portions in addition to reducing tension in areas not needing high tension. Other important advantages include the capability of various laydown patterns of the elastic in conjunction with cross-sectional area variations which can be utilized to improve the seal and fit around a user's legs or thighs without being excessively constricting. Also a controlled tension gradiant can be accomplished by varying the amplitude and pitch of the corrugations at predetermined portions of the backing and/or facing webs. An hour glass pattern of elastic complimantary to the hour glass pattern of a diaper of that configuration rather than a straight line elastic pattern significantly improves the diaper fit around the thighs, especially in diapers for adults.

Some embodiments of the invention involve placement of corrugations, pleats, or folds in specific discrete areas in a substantially inelastic moving web and applying an elastic member under substantially no tension to these areas and other areas having no corrugations. The elastic member can be adhesive coated and applied in a solid state at ambient temperatures or higher until temperatures are achieved wherein the elastic member is fluid or heat softened so that heat sealing takes place with the facing or backing sheet. As a result of use of little or substantially no tension it is practical to apply the elastic member in various patterns other than a straight line to enhance comfort and sealing capabilities of the diaper.

Using the residual heat in the heat softened extrusions for heat sealing eliminates the need, time and machine length required for preheating elastic to heat sealing temperatures.

The term "extruder" as used in the specification includes gear pumps or various forms of positive displacement devices, including a roller extruder as shown in FIG. 12, for pumping through an extrusion die which may be stationary or cyclic or movable in various directions to accommodate both selected band patterns and cross-sections.

The term "substantially unstretched" as used in the specification includes the tension required to feed elastic members into and through an assembly station. Elastic material at heat softened or room temperature condition will not process properly by pushing.

Figure 24:
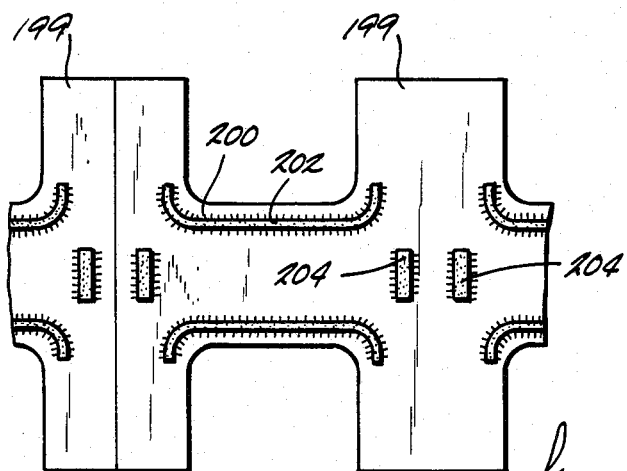
FIG. 24 is a diagrammatic plan view of a web with interconnected diapers having separate elastic ribbons in the crotch and waist band portions.

In addition to variations provided by changing the pattern of the elastic and the cross-section, the selection of areas to be corrugated, including applying elastic ribbons to any area of the diaper, may be appropriate to provide certain advantages. FIG. 24 shows interconnected diapers 199 with a pattern of corrugations 200 and superimposed elastic ribbon 202 which conforms to the outline of the diaper. A transverse waistband strip 204 is provided for tension in the waist. Both the backing and facing sheet can be corrugated.

Figure 25:
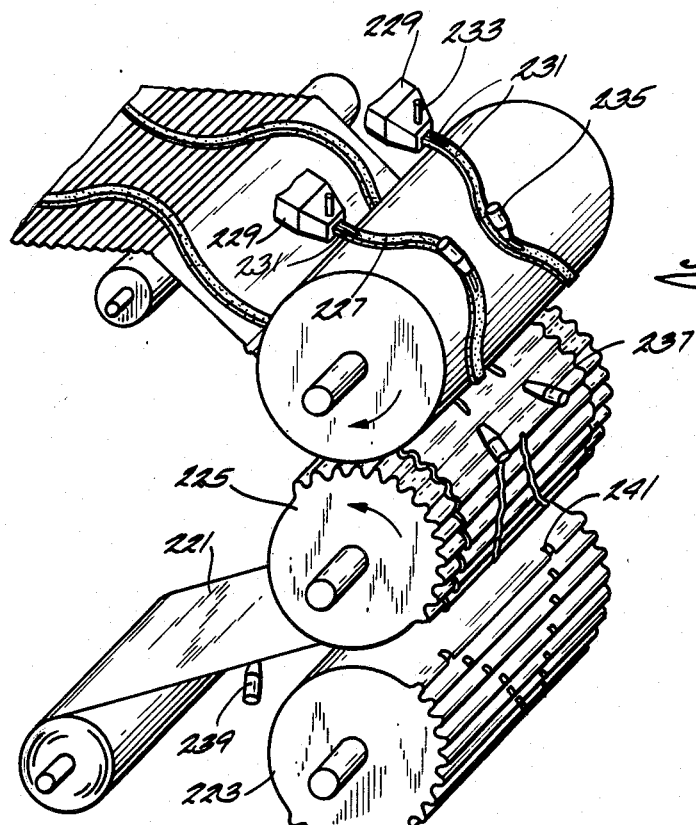
FIG. 25 is a diagrammatic view showing patterned application of an adhesive coated elastic ribbon formed by co-extrusion.

In the preferred embodiments, co-extrusion of the adhesive and elastomeric band are desired. FIG. 25 shows a web 221 corrugated by rolls 223 and 225. The elastic ribbon 227 is extruded from extrusion nozzles 229. A band of adhesive 231 can be simultaneously extruded on the top of the ribbon 227 from the same extruder head 229. The adhesive can be supplied under pressure to the nozzles 229 by inlets 233. This eliminates the registry problems of aligning the adhesive strips with the elastic ribbons at a point remote from the extrusion head.

The application of heated adhesives to heated elastic members by co-extrusion with the use of integral extrusion dies greatly enhances the bond between the adhesive and the elastic member and markedly reduces the process time for the simultaneous cooling of the elastic member adhesive laminate. This method facilitates the use of a greater range of adhesive and elastomeric materials including those of a low cost. Temperature controls, not shown, are used to individually control the temperature of the adhesive and elastic materials.

In addition to co-extruding the adhesive with elastomeric ribbons, adhesive can be additionally added by glue nozzles 235, 237, and 239. Recesses 241 in the roll 223 enable glue to be applied by nozzles 229 without being smeared by the roll 223 during corrugation.

The terms "extruded members", "ribbons", "bands", "elements", "shapes" and "strips" are used interchangeably.

In various of the embodiments of the methods illustrated, the adhesive can be applied to the extruded elastic ribbon before the ribbon has cooled to ambient temperature.

This reduces process time, improves compatibility of adhesive with elastic members and increases surface wetability of the elastic member allowing the use of lower cost adhesives and elastic materials thereby decreasing the cost per unit diaper.

Extrusion of high viscosity extrudate as disclosed herein affords control of the lay down position on the web to provide the elastic ribbon patterns described herein and other appropriate patterns.

The term "rubber" as used herein means "any elastomeric thermoplastic material which is soft, flexible, and elastic."

The term "extrudate" as used herein, means "the final shape of the elastomer which comes out of the die."

I claim:

1. A method for continuously attaching an elastic member to a moving web to impart an elasticized character of a controlled varying intensity along its length, said method comprising the steps of:
   (a) providing an extrusion die with the extrudate therefrom having a preselected variable cross-section;
   (b) controlling the cross-sectional area of the extrudate die while simultaneously extruding a thermoplastic rubber in a heat softened substantially unstretched condition into an assembly station to thereby create an extrudate having a pre-selected variable cross-section to form an elastic ribbon member;
   (c) cooling said elastic ribbon member;
   (d) applying adhesive to said elastic member;
   (e) feeding a web to the assembly station;
   (f) forming corrugations in said web with peaks and valleys;
   (g) adhering the substantially unstretched member to said web across said corrugations by applying the adhesive coated ribbon to the peaks only of the corrugations of the web with the ribbon poritons having greater cross-section being applied to areas of the web requiring greater tension;
   (h) maintaining said elastic member in a substantially unstretched condition contacting only the peaks until the adhesive sets up; and
   (i) drawing the web and elastic member assembly under tension to the corrugations, thereby stretching said elastic member.

2. The method of claim 1, wherein adhesive is applied to the web prior to the step of forming the corrugations and to the corrugations after formed.

3. The method of claim 1, wherein the adhesive is applied intermittently.

4. The method of claim 1, wherein the web is one of a facing and backing sheet for diapers having waistband portions and crotch portions and wherein corrugations are formed in the web portion which will be in the diaper crotch.

5. The method of claim 1, wherein the web is one of a facing and backing sheet for a diaper and the corrugations are formed in narrow bands longitudinally of the web adjacent the side margins of the web.

6. The method of claim 1 wherein the web is one of a facing and backing sheet for a diaper having an hourglass configuration and said elastic member is laid down in a pattern complementary to said configuration to provide elastic tension adjacent the edges of said diapers.

7. The method of claim 1 including the step of providing an extrusion die which can be moved longtidiuinally and laterally of the web and toward and away from the web.

8. The method of claim 1 wherein the web is one of a facing and backing sheet for a diaper and two elastic members are extruded and the spacing between the elastic members is less in the crotch area than in the diaper waistband portion.

9. The method of claim 1, wherein elastic ribbons are extruded on web portions transverse to the direction of web movement to elasticize waistband portions of diapers formed by said web and elastic ribbons are extruded generally longitudinally of the web to form elasticized crotch portions.

10. The method of claim 1, including the step of providing an extrusion head and roller with an arcuate surface on the extrusion head complementary to the surface of the roller.

11. The method of claim 1 including the step of providing means for moving the extrusion die in one of a longitudinal, lateral and toward and away direction with respect to the web.

* * * * *